United States Patent
Stalsberg et al.

(10) Patent No.: US 8,145,296 B2
(45) Date of Patent: Mar. 27, 2012

(54) ADAPTIVE WINDOWING FOR CARDIAC WAVEFORM DISCRIMINATION

(75) Inventors: Kevin J. Stalsberg, White Bear Lake, MN (US); Yanting Dong, Shoreview, MN (US); Scott Meyer, Lakeville, MN (US); Eric K. Enrooth, Lino Lakes, MN (US); Derek D. Bohn, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 408 days.

(21) Appl. No.: 12/538,297

(22) Filed: Aug. 10, 2009

(65) Prior Publication Data
US 2010/0036449 A1   Feb. 11, 2010

Related U.S. Application Data

(63) Continuation of application No. 11/116,578, filed on Apr. 28, 2005, now Pat. No. 7,574,260.

(51) Int. Cl.
  *A61B 5/042* (2006.01)
(52) U.S. Cl. .................. 600/509; 600/515; 607/28
(58) Field of Classification Search .................. 607/28; 600/509, 515; 128/901, 902
  See application file for complete search history.

(56) References Cited

U.S. PATENT DOCUMENTS

| | | | |
|---|---|---|---|
| 3,920,005 A | 11/1975 | Gombrich et al. | |
| 4,023,564 A | 5/1977 | Valiquette et al. | |
| 4,458,692 A | 7/1984 | Simson | |
| 4,680,708 A | 7/1987 | Ambos et al. | |
| 4,878,497 A | 11/1989 | Callaghan et al. | |
| 4,979,507 A | 12/1990 | Heinz | |
| 5,000,189 A | 3/1991 | Throne et al. | |
| 5,184,615 A | 2/1993 | Nappholz et al. | |
| 5,217,021 A | 6/1993 | Steinhaus et al. | |
| 5,222,493 A | 6/1993 | Sholder | |
| 5,271,411 A | 12/1993 | Ripley et al. | |
| 5,273,035 A | 12/1993 | Markowitz et al. | |
| 5,324,310 A | 6/1994 | Greeninger et al. | |

(Continued)

FOREIGN PATENT DOCUMENTS
EP   0468720   1/1992
(Continued)

OTHER PUBLICATIONS

Mitchell I. Cohen et al. *Capture Management Efficacy in children and young adults with endocardial and unipolar epicardial systems.* Europace, vol. 6, pp. 248-255 (2004).

(Continued)

*Primary Examiner* — Carl H Layno
*Assistant Examiner* — Natasha Patel
(74) *Attorney, Agent, or Firm* — Seager, Tufte & Wickhem, LLC

(57) ABSTRACT

Cardiac devices and methods provide adaptation of detection windows used to determine a cardiac response to pacing. Adapting a detection window involves sensing a cardiac signal indicative of a particular type of cardiac pacing response, and detecting a feature of the sensed cardiac signal. The cardiac response detection window associated with the type of cardiac pacing response is preferentially adjusted based on the location of the detected cardiac feature. Preferential adjustment of the detection window may involve determining a direction of change between the detection window and the detected feature. The detection window may be adapted more aggressively in a more preferred direction and less aggressively in a less preferred direction.

21 Claims, 10 Drawing Sheets

U.S. PATENT DOCUMENTS

| | | | |
|---|---|---|---|
| 5,350,410 A | 9/1994 | Kleks et al. | |
| 5,374,280 A | 12/1994 | den Dulk | |
| 5,411,533 A | 5/1995 | Dubreuil | |
| 5,431,693 A | 7/1995 | Schroeppel | |
| 5,443,485 A | 8/1995 | Housworth et al. | |
| 5,447,519 A | 9/1995 | Peterson | |
| 5,534,017 A | 7/1996 | Van Krieken et al. | |
| 5,626,620 A | 5/1997 | Kieval et al. | |
| 5,674,254 A | 10/1997 | van Krieken | |
| 5,683,431 A | 11/1997 | Wang | |
| 5,683,434 A | 11/1997 | Archer | |
| 5,713,933 A | 2/1998 | Condie et al. | |
| 5,779,645 A | 7/1998 | Olson et al. | |
| 5,817,027 A | 10/1998 | Arand et al. | |
| 5,857,977 A | 1/1999 | Caswell et al. | |
| 5,861,013 A | 1/1999 | Peck | |
| 5,871,512 A | 2/1999 | Hemming et al. | |
| 5,873,898 A | 2/1999 | Hemming et al. | |
| 6,038,474 A | 3/2000 | Zhu et al. | |
| 6,052,620 A | 4/2000 | Gillberg et al. | |
| 6,076,014 A | 6/2000 | Alt | |
| 6,101,416 A | 8/2000 | Sloman | |
| 6,115,628 A | 9/2000 | Stadler et al. | |
| 6,128,535 A | 10/2000 | Maarse | |
| 6,134,473 A | 10/2000 | Hemming | |
| 6,163,724 A | 12/2000 | Hemming et al. | |
| 6,169,921 B1 | 1/2001 | KenKnight et al. | |
| 6,175,766 B1 | 1/2001 | Bornzin et al. | |
| 6,192,275 B1 | 2/2001 | Zhu et al. | |
| 6,221,011 B1 | 4/2001 | Bardy | |
| 6,226,551 B1 | 5/2001 | Zhu et al. | |
| 6,238,419 B1 | 5/2001 | Lindgren | |
| 6,270,457 B1 | 8/2001 | Bardy | |
| 6,272,377 B1 | 8/2001 | Sweeney et al. | |
| 6,275,731 B1 | 8/2001 | Zhu et al. | |
| 6,277,072 B1 | 8/2001 | Bardy | |
| 6,280,380 B1 | 8/2001 | Bardy | |
| 6,312,378 B1 | 11/2001 | Bardy | |
| 6,312,388 B1 | 11/2001 | Marcovecchio et al. | |
| 6,324,427 B1 | 11/2001 | Florio | |
| 6,336,903 B1 | 1/2002 | Bardy | |
| 6,345,201 B1 | 2/2002 | Sloman et al. | |
| 6,358,203 B2 | 3/2002 | Bardy | |
| 6,368,284 B1 | 4/2002 | Bardy | |
| 6,393,316 B1 | 5/2002 | Gillberg et al. | |
| 6,398,728 B1 | 6/2002 | Bardy | |
| 6,418,343 B1 | 7/2002 | Zhang et al. | |
| 6,434,417 B1 | 8/2002 | Lovett | |
| 6,434,428 B1 | 8/2002 | Sloman et al. | |
| 6,440,066 B1 | 8/2002 | Bardy | |
| 6,449,503 B1 | 9/2002 | Hsu | |
| 6,456,881 B1 | 9/2002 | Bornzin et al. | |
| 6,466,820 B1 | 10/2002 | Juran et al. | |
| 6,480,734 B1 | 11/2002 | Zhang et al. | |
| 6,505,071 B1 | 1/2003 | Zhu et al. | |
| 6,512,953 B2 | 1/2003 | Florio et al. | |
| 6,567,701 B2 | 5/2003 | Vonk | |
| 6,615,082 B1 | 9/2003 | Mandell | |
| 6,618,619 B1 | 9/2003 | Florio et al. | |
| 6,658,293 B2 | 12/2003 | Vonk | |
| 6,684,100 B1 | 1/2004 | Sweeney et al. | |
| 6,731,983 B2 | 5/2004 | Ericksen et al. | |
| 6,738,669 B1 | 5/2004 | Sloman et al. | |
| 6,885,893 B1 * | 4/2005 | Lu | 607/28 |
| 6,917,832 B2 | 7/2005 | Hutten | |
| 6,950,702 B2 | 9/2005 | Sweeney | |
| 6,973,350 B1 | 12/2005 | Levine et al. | |
| 6,975,904 B1 | 12/2005 | Sloman | |
| 7,027,868 B2 | 4/2006 | Rueter et al. | |
| 7,191,003 B2 | 3/2007 | Greenhut et al. | |
| 7,319,900 B2 | 1/2008 | Kim et al. | |
| 7,369,889 B2 | 5/2008 | Astrom et al. | |
| 7,477,932 B2 | 1/2009 | Lee et al. | |
| 2004/0172065 A1 | 9/2004 | Sih et al. | |
| 2004/0260351 A1 | 12/2004 | Holmstrom et al. | |
| 2005/0004612 A1 | 1/2005 | Scholten et al. | |
| 2005/0131477 A1 * | 6/2005 | Meyer et al. | 607/27 |
| 2005/0131478 A1 | 6/2005 | Kim et al. | |
| 2006/0129196 A1 | 6/2006 | Dong et al. | |

FOREIGN PATENT DOCUMENTS

| | | |
|---|---|---|
| EP | 1291038 | 3/2003 |

OTHER PUBLICATIONS

Splett et al. "Determination of Pacing Capture in Implantable Defibrillators: Benefit of Evoked Response Detection Using RV Coil to Can Vector," *PACE*, vol. 23, pp. 1645-1650, Nov. 2000.

Office Action dated Mar. 28, 2007 from U.S. Appl. No. 11/116,578.
Office Action dated Dec. 26, 2007 from U.S. Appl. No. 11/116,578.
Office Action dated Jul. 24, 2008 from U.S. Appl. No. 11/116,578.
Office Action dated Jan. 11, 2006 from U.S. Appl. No. 10/448,260.
Office Action dated Nov. 16, 2006 from U.S. Appl. No. 10/448,260.
Office Action dated Aug. 8, 2007 from U.S. Appl. No. 10/448,260.
Office Action dated Feb. 5, 2008 from U.S. Appl. No. 10/448,260.
Notice of Allowance dated Apr. 2, 2009 from U.S. Appl. No. 11/116,578, 4 pages.
Interview Summary dated Feb. 2, 2009 from U.S. Appl. No. 11/116,578, 2 pages.
Office Action Response dated Jan. 23, 2009 from U.S. Appl. No. 11/116,578, 11 pages.
Office Action Response dated May 5, 2008 from U.S. Appl. No. 11/116,578, 8 pages.
Office Action dated Apr. 7, 2008 from U.S. Appl. No. 11/116,578, 3 pages.
Office Action Response dated Feb. 25, 2008 from U.S. Appl. No. 11/116,578, 13 pages.
Office Action Response dated Oct. 1, 2007 from U.S. Appl. No. 11/116,578, 20 pages.

* cited by examiner

ADAPTIVE WINDOWING FOR CARDIAC WAVEFORM DISCRIMINATION

RELATED PATENT DOCUMENTS

This is a continuation of U.S. patent application Ser. No. 11/116,578, filed on Apr. 28, 2005 and now issued as U.S. Pat. No. 7,574,260, to which Applicant claims priority under 35 U.S.C. §120, and which is incorporated herein by reference.

FIELD OF THE INVENTION

The present invention relates generally to implantable medical devices and, more particularly, to cardiac devices and methods used in cardiac pacing response determination.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically include circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Detecting if a pacing pulse "captures" the heart and produces a contraction allows the cardiac rhythm management system to adjust the energy level of pace pulses to correspond to the optimum energy expenditure that reliably produces capture. Further, capture detection allows the cardiac rhythm management system to initiate a back-up pulse at a higher energy level whenever a pace pulse does not produce a contraction.

When a pace pulse produces a contraction in the heart tissue, the electrical cardiac signal preceding the contraction is denoted the captured response. The captured response typically includes an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example. The evoked response may be affected by interaction with intrinsic heart activity and resulting in a fusion or pseudofusion response.

A fusion beat is a cardiac contraction that occurs when two cardiac depolarizations of a particular chamber, but from separate initiation sites, merge. At times, a depolarization initiated by a pacing pulse may merge with an intrinsic beat, producing a fusion beat. Fusion beats, as seen on electrocardiographic recordings, exhibit various morphologies, since the merging depolarizations of a fusion beat do not contribute evenly to the total depolarization.

Pseudofusion occurs when a pacing stimulus is delivered on a spontaneous P wave during atrial pacing or on a spontaneous QRS complex during ventricular pacing. In pseudofusion, the pacing stimulus may be ineffective because the tissue around the electrode has already spontaneously depolarized and is in its refractory period.

Noise presents a problem in capture detection processes when the pacemaker mistakenly identifies noise as capture, fusion/pseudofusion, or intrinsic activity. Noise mistakenly identified as capture or fusion/pseudofusion may cause a pacemaker to erroneously withhold backup pacing under loss of capture conditions. Noise mistakenly identified as early intrinsic activity may lead to a premature loss of capture determination during threshold testing.

The present invention provides methods and systems used for enhancing the discrimination of types of cardiac pacing responses, such as those described above, and provides various advantages over the prior art.

SUMMARY OF THE INVENTION

The present invention involves cardiac devices and methods incorporating adaptive windows for cardiac waveform discrimination. An embodiment of the invention involves a method for adjusting detection windows used for detection of various types of cardiac response to pacing. The method includes sensing a cardiac signal associated with the type of cardiac response and detecting a feature of the sensed cardiac signal. The detection window is preferentially adapted based on the location of the detected cardiac signal feature. The detection window may be defined, for example, in terms of amplitude and time, or may be defined in terms of additional or alternative parameters. Adaptation of the detection window may involve adjusting the location, size, shape, area, or boundaries of the detection window, for example.

According to one aspect of the invention, the detection window may be preferentially adjusted based on a direction of change between the detection window and the location of the detected feature. The detection window may be adjusted more aggressively in a preferred direction of change and less aggressively in a less preferred direction of change. In another implementation, the detection window may be adapted based on a relationship between the location of the detected feature and a detection window limit. For example, features may be selectively used to update the detection window. If a feature is located close to or at a detection window limit, for example, it may not be used for detection window update.

A system for adapting detection windows used for cardiac response discrimination in accordance with embodiments of the present invention includes a sensing system configured to sense cardiac signals following pacing pulses delivered to a heart. A processor is coupled to the sensing system and is configured to detect a feature of the cardiac signals. The processor is configured to preferentially adjust the detection window based on the location of the cardiac signal feature.

For example, in one implementation, the processor may be configured to preferentially adjust the detection window based on a direction of change between the detected feature location and the cardiac response detection window position. Additionally, or alternatively, the processor may adjust the detection window based on the location of a cardiac signal feature with respect to a detection window limit.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
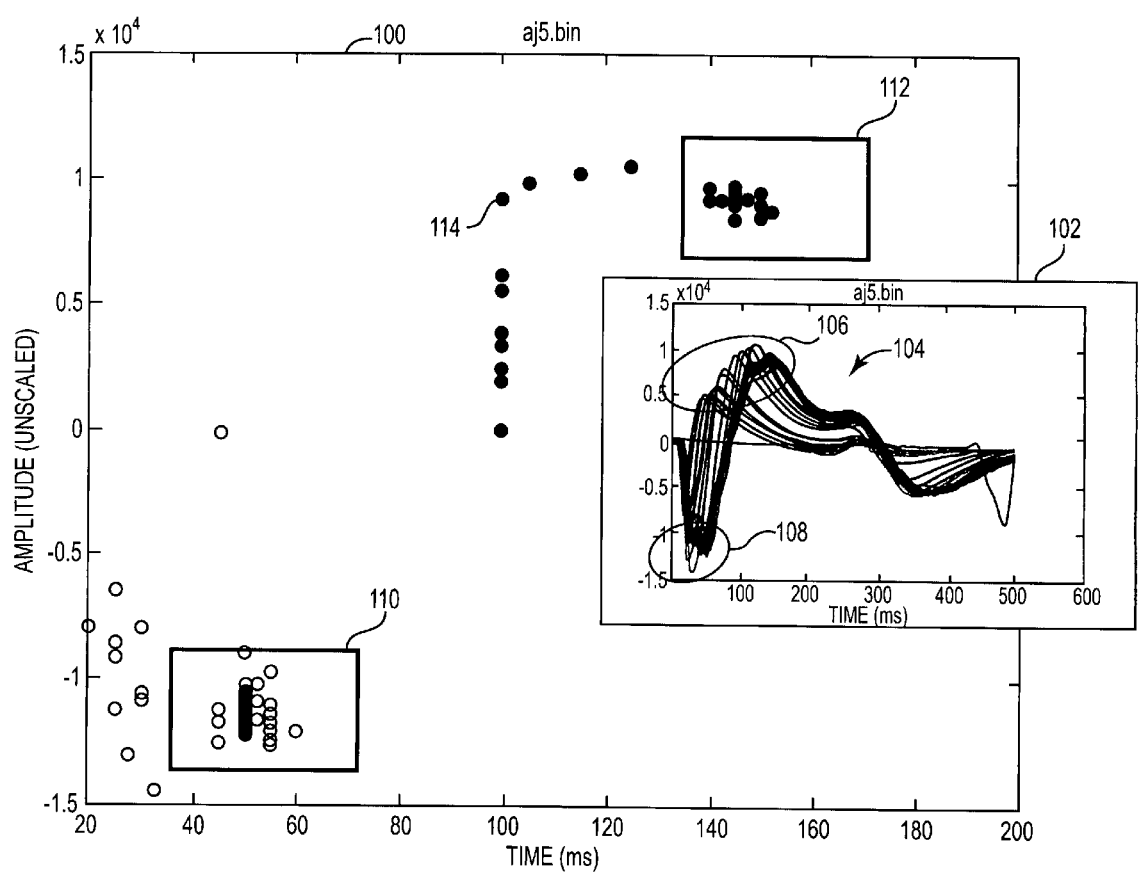
FIG. 1A is a graph illustrating cardiac waveform portions and their associated peak information, showing clustering and bounding of capture detection windows in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

Cardiac response classification may be implemented by a pacemaker or other cardiac rhythm management device to determine whether an applied electrical pacing stimulus captures the heart. The systems and methods described herein are related to the use of cardiac signal features to discriminate between various types of cardiac responses to pacing. Discrimination between cardiac pacing responses may involve discrimination between capture and fusion and/or non-capture with or without intrinsic activation. The approaches of the present invention provide for enhanced capture threshold testing and/or beat to beat automatic capture verification.

Several functions of cardiac devices rely on the heart response consistency. For example, automatic capture threshold testing and/or automatic capture verification algorithms may rely on templates of the heart's response as the basis for determining whether a future pacing stimulus produces a particular type of response. However, the cardiac responses may vary across patients and change over time.

Templates representative of various types of cardiac responses may comprise one or more detection windows. The detection windows are compared to a cardiac signal following delivery of a pacing pulse to determine the response to pacing. Devices and methods in accordance with the present invention adapt one or more detection windows as the patient's signal morphology changes over time. Cardiac response detection windows may be adapted based on prior and/or ongoing feature measurements that are consistent with a current template, for example.

In accordance with embodiments of the invention, a detection window may be preferentially adapted based on the location of a cardiac signal feature. In some implementations, the location of the cardiac signal feature and the location and boundaries of the capture detection windows may be defined in terms of amplitude and time, although additional or alternative parameters may be used. The preferential adaptation of a detection window may occur by modifying the location, shape, area or other characteristics or parameters of the detection window in accordance with embodiments of the invention. In one implementation, preferential adaptation of a detection window may be based, for example, on the direction of change between the detection window and the location of a measured cardiac signal feature. The detection window may be adapted more aggressively (higher rate of adaptation) in a more preferred direction and less aggressively (lower rate of adaptation) in a less preferred direction.

Allowing for different adaptation rates of a detection window may accommodate asymmetry in template dimensions, and preferred directional change/response to maintain operational limits, such as safety limits. Adapting detection windows within operational limits may insure proper classification through a feature's full measurement range, and help to avoid problems such as those associated with small amplitude captured response signals and sense amplifier saturation limits.

According to various aspects of the invention, features may be used to adapt the detection window and to compress the boundary of a detection window against an operational limit. In some implementations, features may not be used to update a detection window if the features fall too close to a detection window limit.

Consider the case where one or more peaks of the cardiac signal are cardiac signal features used to detect a captured response. One or more capture detection windows may be defined as a template associated with a captured response. The capture detection windows are regions, having coordinates of amplitude and time, bounding clustered signal peaks of multiple cardiac signals under conditions of captured response, as is illustrated in FIG. 1A. The graphs in FIG. 1A illustrate cardiac waveform portions and their associated peak information, showing clustering and bounding of capture detection windows in accordance with embodiments of the present invention.

A graph 100 plots the positive and negative peaks of the cardiac waveforms graphed in an inset graph 102. The inset graph 102 shows several cardiac waveforms 104 including positive peaks 106 and negative peaks 108. The amplitudes and times associated with the peaks of the cardiac waveforms 104 in graph 102 provide the coordinate system measurements for the points plotted in the graph 100.

The graph 100 includes a first capture detection window 110 associated with negative peaks of a captured response and a second capture detection window 112 associated with positive peaks of a captured response. The capture detection windows 110, 112 are used to discriminate beats corresponding to capture from other types of pacing responses. If a waveform's negative peak falls within the first capture detection window 110 and a waveform's positive peak falls within the second capture detection window 112, the beat is associated with a captured response. Non-captured beats, such as fusion beats or intrinsic beats, have peaks that fall outside one or both the windows 110, 112.

For example, a point 114 of the graph 100 corresponds to a peak value of a cardiac response signal that does not correspond to a captured beat. The measured coordinates of peak time and peak amplitude of the point 114 fall outside the second capture detection window 112.

Figure 1B:
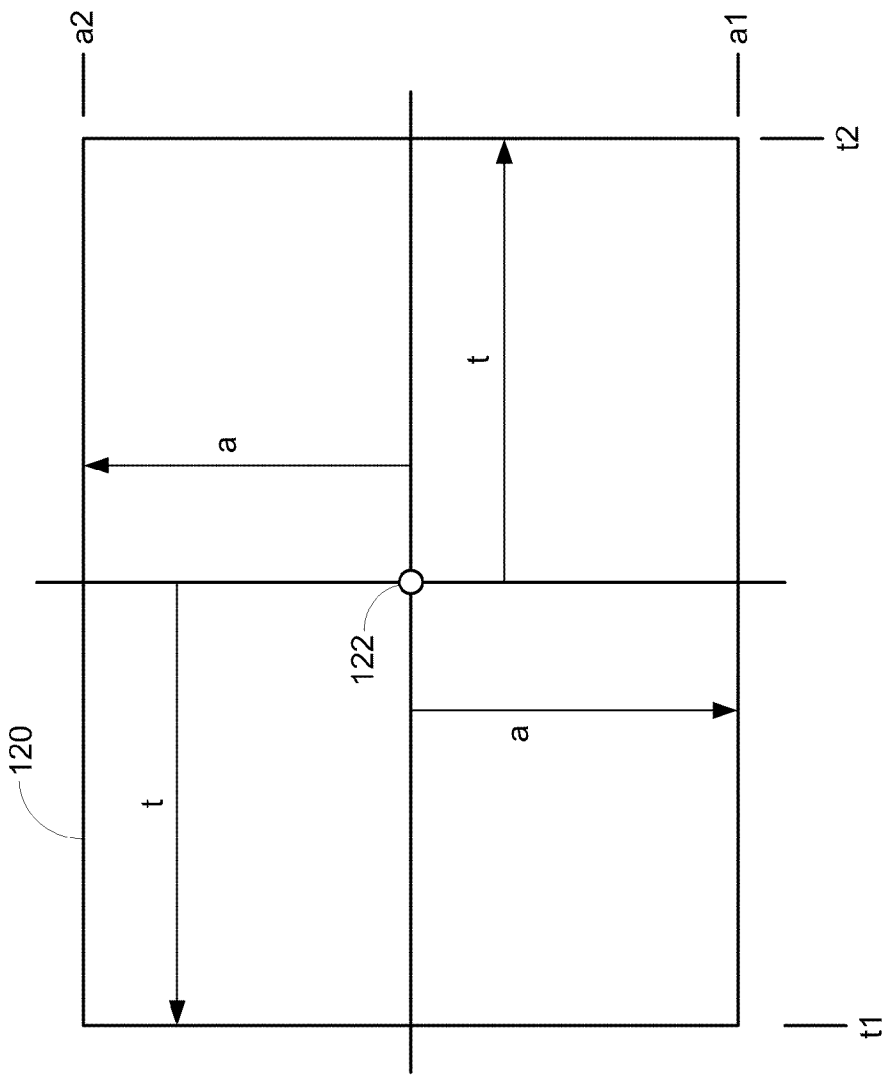
FIG. 1B illustrates a capture detection window, a reference point, and their associated coordinate information.

FIG. 1B illustrates a capture detection window 120, having a reference point 122, and associated coordinate information. The capture detection window 120 may have a height defined as 2$a$, spanning an amplitude a above and below the reference point 122. An amplitude a1 corresponds to the reference point 122 y-axis coordinate minus a, and an amplitude a2 corresponds to the reference point 122 y-axis coordinate plus a. The reference point 122 is illustrated in FIG. 1B at the middle of the amplitude range of the capture detection window from a1 to a2, but is not limited to this relationship. The reference point 122 may have any defined relationship to the upper and lower bounds of the capture detection window 120, and the relationship may change over time.

For example, as the capture detection window 120 upper bound a2 approaches a physical or desired limit of amplitude, the relationship between the reference point 122 and the upper bound a2 may change, in order to clamp the capture detection window 120 upper bound a2 to the desired amplitude limit. In another embodiment, after the capture detection window 120 upper bound a2 reaches a limit, the capture detection window 120 may be restricted from moving higher. In another embodiment, after the capture detection window 120 upper bound a2 reaches a limit, the upper bound a2 of the capture detection window may be restricted from further modification, while modification of the lower amplitude bound and/or time boundaries t1 and t2 may continue. In a further embodiment, as the capture detection window 120 upper bound a2 approaches a physical or desired limit of amplitude, the rate of change of the upper bound a2 and/or the position of the reference point 122 may be altered to compress or limit the adaptation of the capture detection window 120. In another embodiment, the sensitivity and/or rate at which the capture detection window 120 is adapted may be based on a preferred direction, amplitude, or other criteria. In yet another embodiment, current feature measurements may be selectively used to update the capture detection window. For example, if the feature location is within a predetermined distance of a detection window limit, then the feature may not be selected to adjust the capture detection window.

For example, the capture detection window 120 may be adapted using an algorithm that accounts for a preferred direction of movement and/or adaptation for the capture detection window 120. One example involves using a filtering of the peak amplitude that is applied when criteria are met. A filtering equation may be used, such as:

$$\text{New\_Amplitude} = (1-\alpha) \cdot \text{Old\_Amplitude} + \alpha \cdot \text{Current\_Peak\_Amplitude}$$

where the update coefficient, $\alpha$, determines the significance of the newest measured peak amplitude contribution to the filtered value. The filtered value may then be used as the amplitude reference point for the capture detection window. In some embodiments, the system may determine whether to use a current peak amplitude for capture detection window update. For example, if the current peak amplitude is close to or equals the upper limit, then the current peak amplitude may not be used to update the capture detection window.

The capture detection window 120 may have a width defined as spanning from t1 to t2, where t1 and t2 are respectively referenced to the left and right of the reference point 122. A time t1 corresponds to the reference point 122 x-axis coordinate minus t, and a time t2 corresponds to the reference point 122 x-axis coordinate plus t. The reference point 122 is illustrated in FIG. 1B at the middle of the time range from t1 to t2, but is not limited to this relationship. The reference point 122 may have any defined relationship to the left and right bounds of the capture detection window 120, and the relationship may change over time. The minimum, maximum, sensitivity, and/or rate at which t1 and/or t2 are adapted may also be based on a preferred direction, limits, or other criteria, similarly to amplitude bounds a1 and a2.

Time values may be filtered using a differential update coefficient, which may be based on the relative position of the current time measurement relative to the capture detection window time reference. Using the differential update coefficient may account for detection window limits, where the time boundary for a detection window may have a tighter limit on one side and a looser limit on the other side, providing the ability of the window to move in a preferred direction. By using a preferred direction sensitivity, significant shifts in the window caused by a few large signals in an undesirable direction may be mitigated.

Figure 1C:
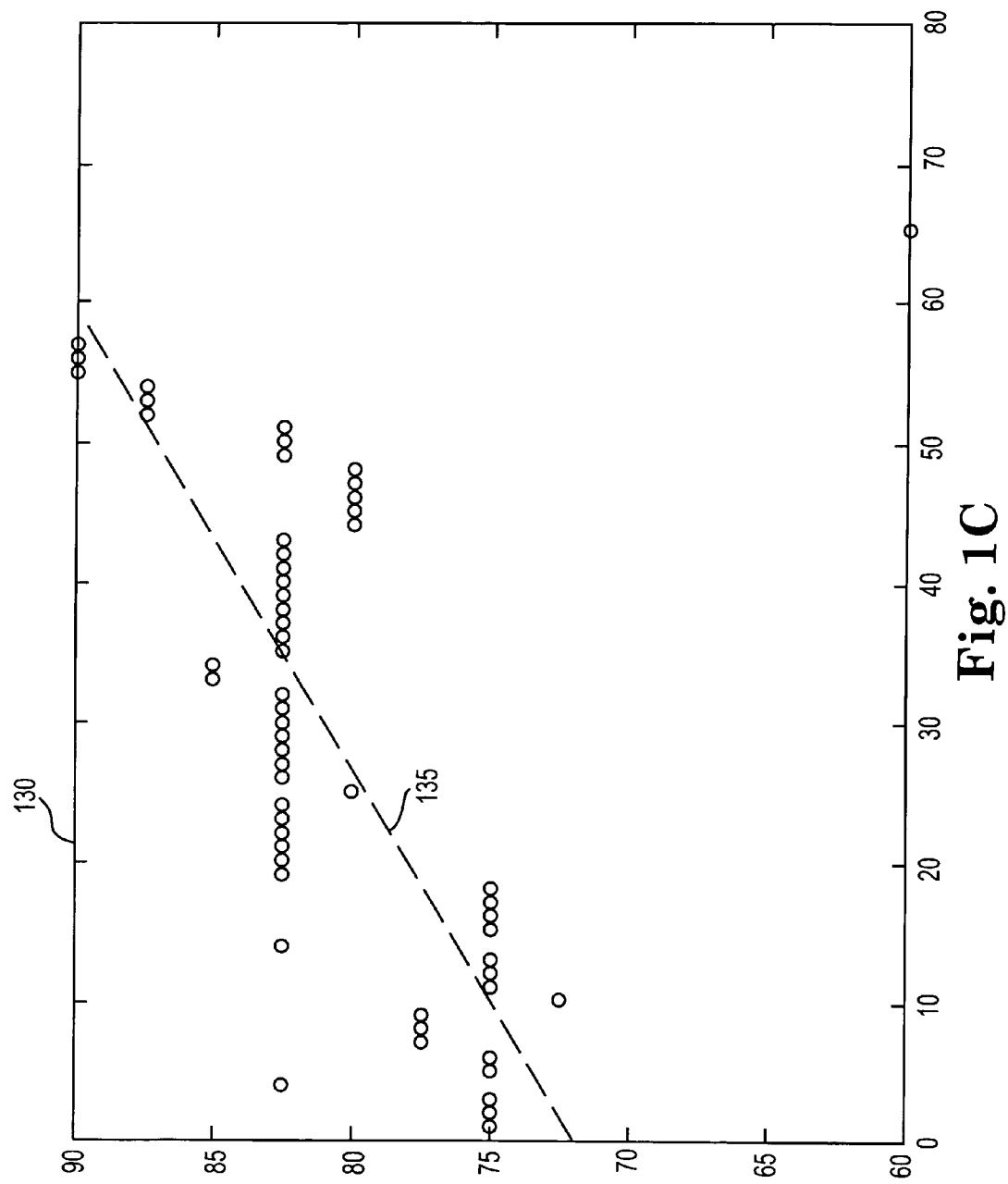
FIG. 1C is a graph of cardiac waveform peak information illustrating peak location drift.

FIG. 1C is a graph 130 of cardiac waveform peak information illustrating peak location drift. Signal drift may be accounted for by adapting detection windows in accordance with the present invention. The graph 130 plots the capture response negative peak time on the ordinate and successive cardiac cycle count in the abscissa. As is seen generally by the line approximation 135 through the negative capture peaks, the signal is drifting over time. If the capture detection window is adapted in accordance with embodiments of the present invention, the window may be shifted along with the creep in the signal peaks to provide improved discrimination capabilities.

For example, as with capture detection window amplitude, the capture detection window time reference may be adapted using a filtering of the peak time that is applied when criteria are met. A filtering equation may be used, such as:

New time=$(1-\beta)\cdot$Old_Time+$\beta\cdot$Current_Peak_time where the update coefficient, $\beta$, determines the significance of the newest measured peak time contribution to the filtered value. The filtered value may then be used as the newly adapted time reference point for the capture detection window. Different $\beta$-values can be used to apply directional preference, determined by the location of the current peak time relative to the time reference of the appropriate capture detection window.

In various embodiments, multiple detection windows may be adapted, such as by using equations similar to those above. Consider the case where a template involves a first detection window associated with a first cardiac signal feature, e.g., a first peak, and a second detection window associated with a second cardiac signal feature, e.g., a second peak. The first and second detection windows may be adjusted based on the location of the first and second cardiac signal features. As will be apparent to those skilled in the art, any number of parameters and any number of multi-variable detection windows in any combination may be used without departing from the scope of the present invention.

Figure 2A:
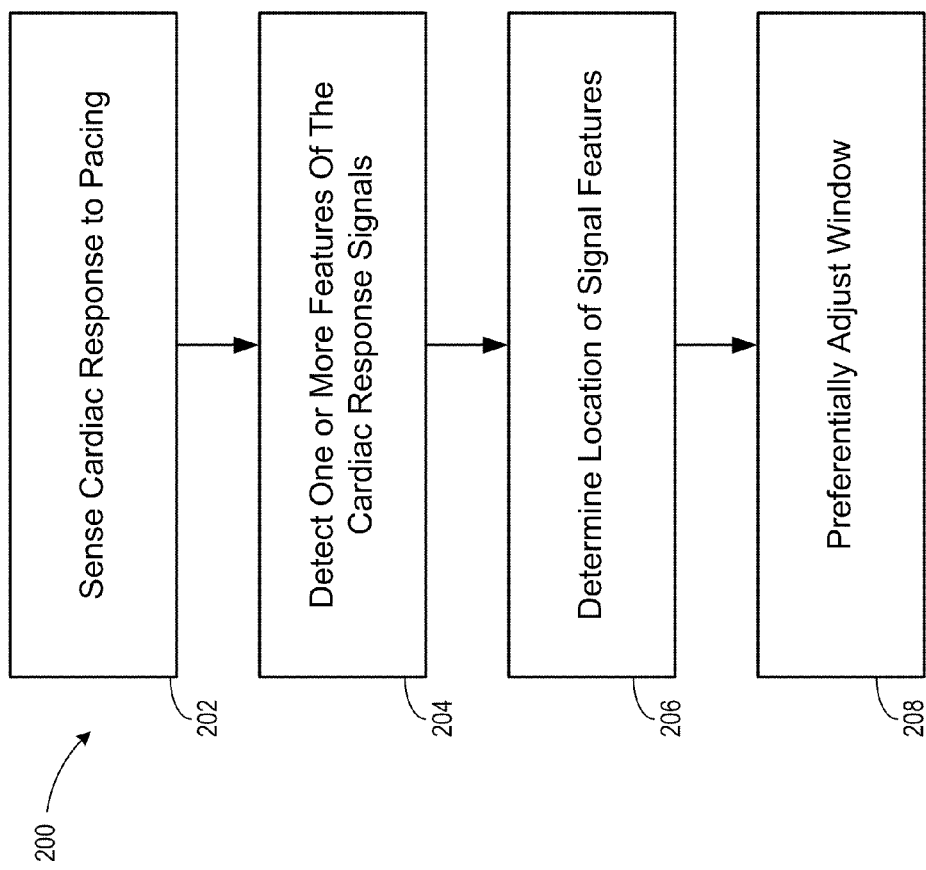
FIG. 2A is a flowchart of a method of adapting windows for cardiac waveform discrimination in accordance with embodiments of the invention.

FIG. 2A is a flowchart of a method 200 of adapting detection windows for cardiac response discrimination in accordance with embodiments of the invention. Cardiac signals from pacing pulses are sensed 202. Cardiac signal features 204 are detected, and measurements are made of cardiac signal feature parameters, such as by sensing for a peak amplitude, zero crossing, inflection point, QRS width, or other measurements. Locations of one or more cardiac signal features are determined 206. For example, a location of a signal feature may be defined by a current measurement of the Cartesian peak amplitude and peak time values of the cardiac signal. The amplitude and time values may be compared to boundaries associated with a detection window. If the feature location falls within the boundaries of a detection window, then the detection window may be preferentially adjusted 208 based on the current feature location in accordance with the present invention.

For example, the reference point of a detection window may be defined as a running average value of all signal peak amplitudes and peak times for the last sixty-four cardiac waveforms peaks that fell within the detection window. If the current waveform peak falls within the detection window, the current peak amplitude value and peak time may be averaged with the last sixty-three respective values, and the oldest value may be dropped from the running average. The use of sixty-four as the running average number is only an example of a useful average to improve the signal to noise ratio, and is not intended to be the only useful value or limiting in any way.

By utilizing a running average, the window will continuously adapt to the most recent patient responses. Limits of the detection window may be clamped and/or the reference point and/or boundary values may be compressed in accordance with embodiments of the present invention to account for operational limits of a patient implantable medical device (PIMD). The detection window parameters including, for example, boundary locations, size, shape, area, reference point location, and the like, may be constrained by desired or required maximum and/or minimum values, and/or preferential window movement directions to limit window movement magnitudes or rates in particular directions.

Figure 2B:
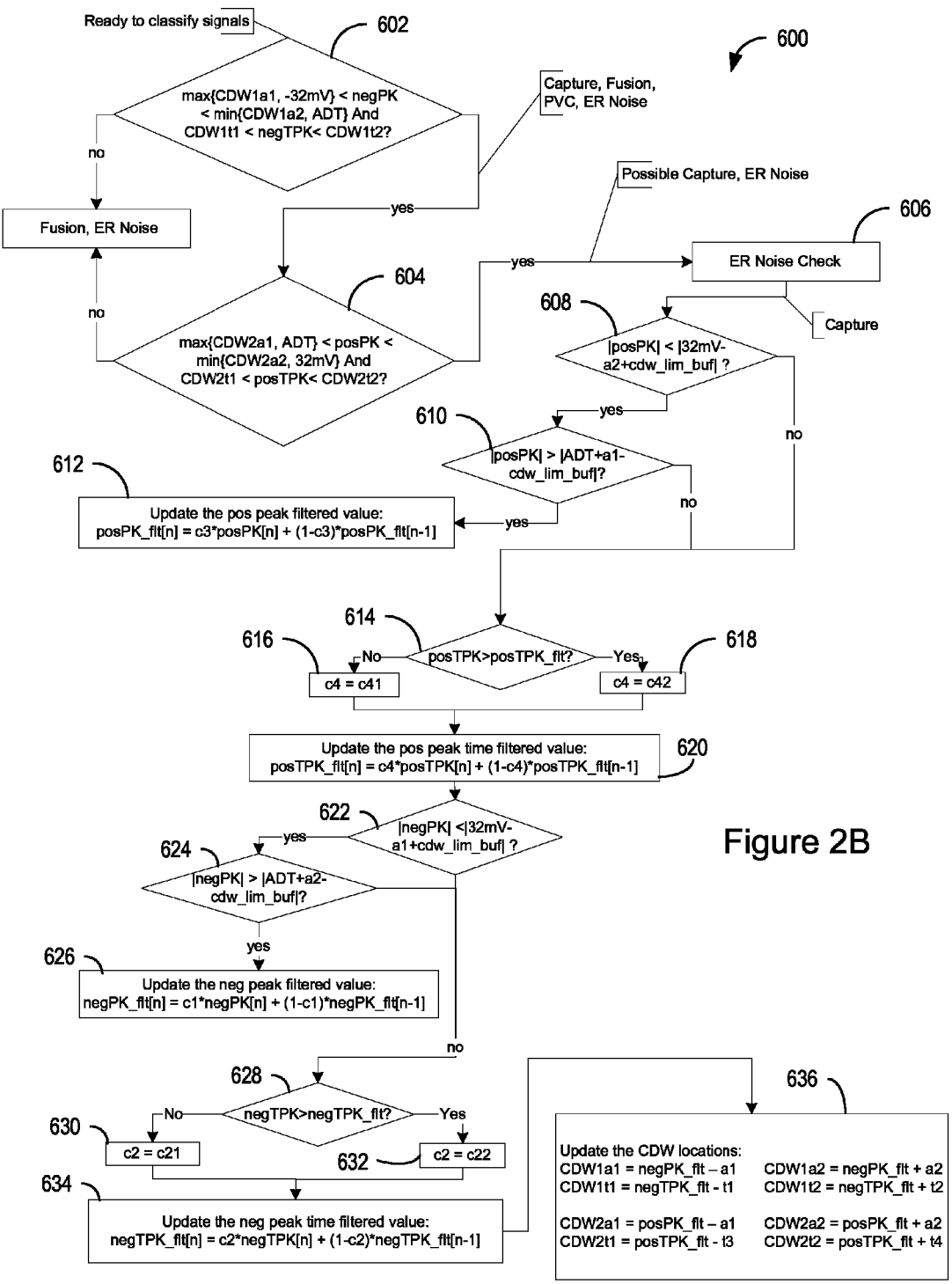
FIG. 2B is a flowchart of a functional implementation of a method using cardiac waveform clustering for adapting windows for cardiac waveform discrimination in accordance with embodiments of the invention.

FIG. 2B is a flowchart of a functional implementation of a method 600 for adapting capture detection windows for cardiac waveform discrimination in accordance with embodiments of the invention. Although FIG. 2B illustrates processes as applied to capture detection windows, other types of detection windows, such as those used for the detection of fusion or early intrinsic beats, may be similarly adapted.

If a signal is ready to be classified, checks 602 and 604 are made to determine if the negative and positive peak features of the cardiac response signals reside in the respective capture detection windows, thereby determining a capture response. A capture response noise check 606 is then performed to eliminate the possibility that noise interfered with the capture determination. Once a capture response is determined, the current peak information can be considered for adaptation of the current capture detection window (CDW) reference location.

The checks for capture determination 602 and 604 also provide adaptation limits for the CDW against the peak feature's full measurement range, essentially allowing the CDW to compress against a designated measurement range, and thereby allowing proper classification throughout that measurement range.

The negative peak check 602, may be made to determine if a negative peak, negPK, and a negative peak timing, negTPK, are within a first capture detection window, CDW1, that may be located against maximum or minimum measurement limits determined by the equations:

$$\max\{CDW1a1, -32\ mV\} < negPK < \min\{CDW1a2, ADT\}$$

and $$CDW1t1 < negTPK < CDW1t2$$

where CDW1$a$1 and CDW1$a$2 are the values of a1 and a2 respectively for the CDW1, and CDW1$t$1 and CDW1$t$2 are the values of t1 and t2 respectively for CDW1, and ADT is an activity detection threshold designating a minimum expected response level. The maximum and minimum operations are used to asymmetrically compress CDW1 against the maximum and minimum of a desired negative peak amplitude measurement range: a –32 mV amplifier saturation and a –2 mV ADT level respectively, in this example. If current negative peak values are outside the designated ranges, they may not be passed to the later CDW adaptation operations. The maximum and minimum operations also prevent later computed filtered peak and time values that are used to adapt the CDW1 reference point, from exceeding the desired negative peak amplitude measurement range, thereby limiting CDW adaptation.

If the signal passes the check 602, then a positive peak check 604 is made to determine if a positive peak amplitude, posPK, and a positive peak timing, posTPK, are within a second capture detection window, CDW2, that may also be located against maximum or minimum measurement limits determined by the equations:

$$\max\{CDW2a1, ADT\} < posPK < \min\{CDW2a2, 32\ mV\}$$

and $$CDW2t1 < posTPK < CDW2t2$$

where CDW2$a$1 and CDW2$a$2 are the values of a1 and a2 respectively for the CDW2, and CDW2$t$1 and CDW2$t$2 are the values of t1 and t2 respectively for CDW2. Again, the maximum and minimum operations are used to asymmetrically compress CDW2 against the maximum and minimum of a desired peak amplitude measurement range: a 32 mV amplifier saturation and a 2 mV ADT level respectively, in this example. Again, if current positive peak values are outside the designated ranges, they may not be passed to the later CDW adaptation operations. The maximum and minimum operations prevent later computed filtered peak and time values that are used to adapt the CDW2 reference point, from exceeding the desired positive peak amplitude measurement range, thereby limiting CDW adaptation.

If the signal passes the checks 602 and 604, an ER noise check 606 is performed to eliminate the possibility that noise interfered with the capture determination. For example, to avoid ER noise detection as capture, the additional peak information is used to check for multiple peaks in wrong places. Given capture is indicated, if other peaks are inconsistent with normal morphology, then ER noise is indicated rather than capture and adaptation of the capture detection window would be avoided.

Once capture is determined, then the signal may be used to adapt the capture detection window(s) in accordance with the present invention. As noted earlier, checks 602 and 604 limit CDW adaptation such that the CDW reference point will not move outside of designated measurement ranges. In this case, the entire upper or lower portions of the CDW are allowed to compress against the respective upper and lower limits of the measurement range. Additional checks 608, 610, 622, and 624 may be put in place to control the amount of CDW compression allowed against designated measurement limits.

Considering the positive peak information first, a determination 608 is made using the equation:

$$|posPK|<|32\ mV-a2+CDW\_lim\_buf|$$

where 32 mV is the maximum of the positive measurement range, a2 is the more positive direction CDW amplitude offset from its reference, and CDW_lim_buf is a predetermined compression limit that may be less than a2. This check prevents any current posPK values within (a2−CDW_lim_buf) of the range maximum, from being used to adapt the CDW2 reference point, thereby limiting CDW adaptation and the compression against the positive measurement range maximum to 32 mV−a2+CDW_lim_buf. If found in the affirmative, then the minimum of the positive measurement range must be considered next, 610, otherwise adaptation for CDW2 is bypassed. Thus, still considering the positive peak information, a decision 610 is made using the equation:

$$|posPK|>|ADT+a1-CDW\_lim\_buf|$$

where ADT is an Activity Detection Threshold designating a minimum expected response level, a1 is the less positive direction CDW amplitude offset from its reference, and CDW_lim_buf is a predetermined compression limit that may be less than a1. This check prevents any current posPK values within (a1−CDW_lim_buf) of the range minimum, from being used to adapt the CDW2 reference point, thereby limiting CDW adaptation and the compression against the positive measurement range minimum to −CDW_lim_buf.

In one example, a1 and a2 may be set equal to about 4 mV for CDW amplitude offsets, and CDW_lim_buf, which defines how much the CDW can be asymmetrically compressed against the minimum/maximum boundaries, may be set equal to about 1 mV.

Given checks 608 and 610 are found in the affirmative, then the CDW2 amplitude reference point is adjusted, 612, using the equation:

$$posPK\_flt[n]=c3*posPK[n]+(1-c3)*posPK\_flt[n-1]$$

where posPK[n] is the current peak amplitude measurement, posPK_flt[n−1] is the previous amplitude reference for CDW2, posPK_flt[n] is the updated amplitude reference point for CDW2, and c3 is the coefficient that determines how much the current peak amplitude measurement contributes to the update. Thus, update 612 performs a recursive low-pass filter value of the peak amplitude if the amplitude is in an acceptable range as determined by checks 602, 604, 608, and 610. If the update 612 is not performed, the CDW amplitude reference stays at a reasonable extreme. In some implementations, amplitude adjustments have limited value and c3 may be set to zero or a minimal value.

Independent of CDW2 reference amplitude adaptation, the CDW2 reference time is adjusted next. In this case a directional preference is established based on whether or not the current positive peak time information is before or after the CDW2 time reference point, posTPK_flt. A check 614 is performed using the equation:

$$posTPK>posTPK\_flt$$

Check 614 compares the current positive peak time to a CDW peak time reference point, posTPK_flt, and, depending on the outcome of the comparison, defines 616, 618 the variable c4. Depending on the outcome of check 614, variable c4 may be defined 616 as c4=c41 or may be defined 618 as c4=c42. Variable c4 is the coefficient that determines how much the current peak time measurement contributes to the CDW time reference point update, 620. The CDW time reference point update may be performed using the equation:

$$posTPK\_flt[n]=c4*posTPK[n]+(1-c4)*posTPK\_flt[n-1]$$

where posTPK[n] is the current peak time measurement, posTPK_flt[n−1] is the previous time reference for CDW2, posTPK_flt[n] is the updated time reference point for CDW2, and c4 is as defined above. A larger c4 value will establish preference toward the current peak time value and thereby a directional preference as established by the check 614. For this example, the window is asymmetric in time about the time reference value: referencing FIG. 1B, t2>t1 or there is a larger time delta when advancing in time versus retarding in time. Coefficient, c4, is adjusted, 616 and 618, to advance the CDW reference location in time more slowly than retarding in time to prevent large movement of the window due to current time values at the time extreme of the CDW. For discussion purposes, c41 may be set equal to about 0.15, and c42 may be set equal to about 0.05, illustrative of reasonable numbers in this example. Thus, update 620 performs a directionally preferenced recursive low-pass filter value of the peak time if the time is in an acceptable range as determined by check 604.

A similar check and adjustment process as described for positive peak amplitude and time, 608 through 620, is now performed on the negative peak amplitude and time regarding CDW1. A check 622 is performed using the equation:

$$|negPK|<|32\ mV-a1+CDW\_lim\_buf|$$

and a check 624 is performed using the equation:

$$|negPK|>|ADT+a2-CDW\_lim\_buf|$$

where 32 mV is the absolute value of the minimum of the negative measurement range, ADT is an Activity Detection Threshold designating the absolute value of the maximum of the negative measurement range, a2 is the more positive direction CDW amplitude offset from its reference, a1 is the less positive direction CDW amplitude offset from its reference, and CDW_lim_buf is a predetermined compression limit that may be less than a1 and a2. These checks prevent any current negPK values within (a1−CDW_lim_buf) of the range minimum and (a2−CDW_lim_buf) of the range maximum, from being used to adapt the CDW1 reference point, thereby limiting CDW adaptation and the compression against the negative measurement range extremes to CDW_lim_buf.

Again, in this example, a1 and a2 may be set equal to about 4 mV for CDW amplitude offsets, and CDW_lim_buf, which defines how much the CDW can be asymmetrically compressed against the minimum/maximum boundaries, may be set to about 1 mV, for example.

Given checks 622 and 624 are found in the affirmative, then the CDW1 amplitude reference point is adjusted, 626, using the equation:

$$negPK\_flt[n]=c1*negPK[n]+(1-c1)*negPK\_flt[n-1]$$

where negPK[n] is the current negative peak amplitude measurement, negPK_flt[n−1] is the previous amplitude reference for CDW1, negPK_flt[n] is the updated amplitude reference point for CDW1, and c1 is the coefficient that determines how much the current peak amplitude measurement contributes to the update. Thus, update 626 performs a recursive low-pass filter value of the negative peak amplitude if the amplitude is in an acceptable range as determined by checks 602, 604, 622, and 624. If the update 626 is not performed, the CDW1 amplitude reference stays at a reasonable extreme. In some implementations, amplitude adjustments have limited value. In these cases, c1 may be set to zero or a minimal value.

Independent of CDW1 reference amplitude adaptation, the CDW1 reference time is adjusted next. In this case, a directional preference is again established based on whether or not the current negative peak time information is before or after the CDW1 time reference point, negTPK flt. A check 628 is performed using the equation:

$$negTPK>negTPK\_flt$$

to compare the current negative peak time to a CDW peak time reference point, negTPK_flt. Depending on the outcome of the comparison, the variable c2 may be defined 630 as c2=c21 or may be defined 632 as c2=c22. Variable c2 is the coefficient that determines how much the current peak time measurement contributes to the CDW time reference point update, 634. The CDW time reference point update may be performed using the equation:

$$negTPK\_flt[n]=c2*negTPK[n]+(1-c2)*negTPK\_flt[n-1]$$

where negTPK[n] is the current negative peak time measurement, negTPK_flt[n−1] is the previous time reference for CDW1, negTPK_flt[n] is the updated time reference point for CDW1, and c2 is as defined above. As with c4, a larger c2 value will establish preference toward the current peak time value and thereby a directional preference as established by the check 628. For this example, the window is symmetric in time about the time reference value: referencing FIG. 1B, t2=t1. Coefficient, c2, is adjusted, 630 and 632, to advance the CDW reference location in time more slowly than retarding in time. For discussion purposes, c21 may be set equal to about 0.15, and c22 may be set equal to about 0.05 here, illustrative of reasonable numbers in this example. Thus, update 634 performs a directionally preferenced recursive low-pass filter value of the negative peak time if the time is in an acceptable range as determined by check 602.

To complete the illustrative method 600, the updated values of the CDWs may be defined as:

$$CDW1a1=negPK\_flt-a1 \quad CDW1a2=negPK\_flt+a2$$

$$CDW1t1=negTPK\_flt-t1 \quad CDW1t2=negTPK\_flt+t2$$

$$CDW2a1=posPK\_flt-a1 \quad CDW2a2=posPK\_flt+a2$$

$$CDW2t1=posPK\_flt-t3 \quad CDW2t2=posPK\_flt+t4$$

The CDWs are adjusted relative to the filtered peak and peak time values, which are the CDW reference points, for every cycle where capture is determined. Some values may not actually need to be computed, as the earlier CDW boundary checks can be done against the offset filter values directly. These calculations may allow the CDW boundaries to extend beyond the maximum/minimum limits of the measurement ranges, but the earlier CDW boundary checks for capture detection and compression limits may be applied to define the maximum/minimum rules that asymmetrically compresses the CDW(s) against the maximum/minimum limits, such as are compressed per a definable compression limit: CDW_lim_buf. For example, dimensional constants may be set as follows:

a1 and a2 may be about 4 mV;
t1 may be about 10 ms;
t2 may be about 15 ms, (with the additional constraint that t1+t2 equal about 25 ms);
t3 may be about 10 ms; and
t4 may be about 50 ms.

Figure 3:
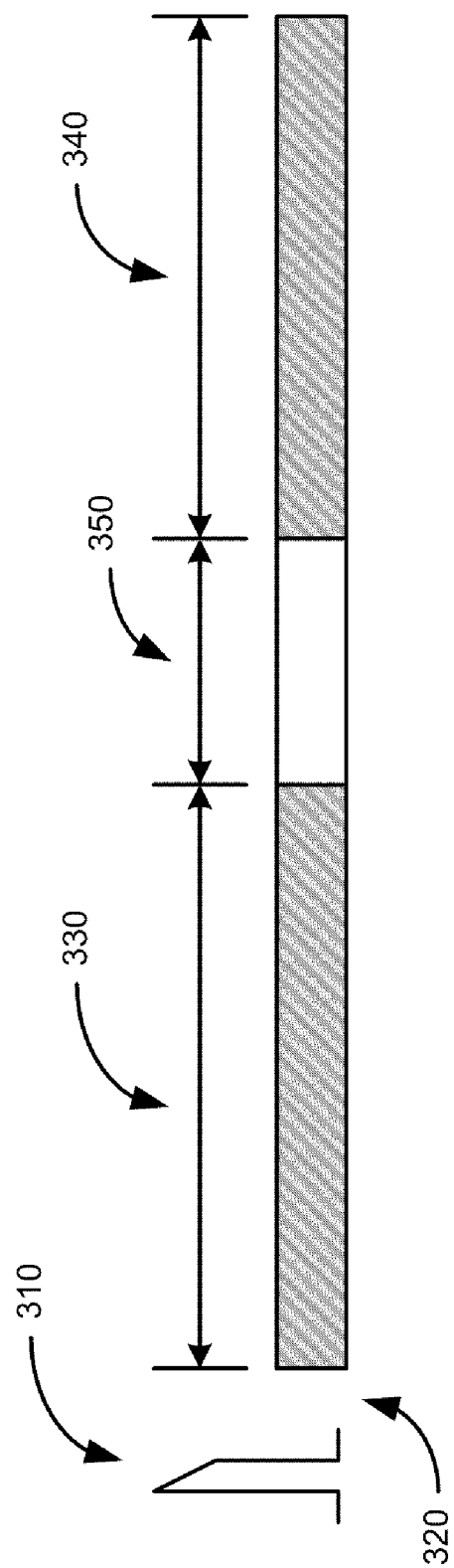
FIG. 3 is a diagram illustrating time intervals that may be used for adapting windows for cardiac waveform discrimination in accordance with embodiments of the invention.

In some implementations, pacing response classification may involve sensing cardiac signals associated with pacing pulses in one or more classification intervals before and/or after the pacing pulse. FIG. 3 illustrates one example of classification intervals that may be implemented for cardiac response classification and detection window adaptation in accordance with embodiments of the invention. A pacing stimulation 310 is delivered to the heart, for example, to the right ventricle. The cardiac signal is blanked for a period of time 320, typically about 0 milliseconds to about 40 milliseconds, following the delivery of the pacing stimulation 310. After the blanking period 320, a first time interval 330 is initiated. The duration of the first time interval 330 may be a programmable duration, for example, less than about 325 milliseconds.

The cardiac signal associated with the pacing pulse is sensed during the first time interval 330. If the magnitude of the cardiac signal does not exceed a threshold in the first time interval 330, then the cardiac response may be classified as a noncaptured response. If the cardiac signal exceeds a threshold value, then various features of the cardiac signal may be detected and used for detection window creation, matching, or adaptation. In some cases, sensing of the cardiac signal may be extended to additional time intervals, such as the second time interval 340. The second time interval 340 may be programmable, and may have a duration less than about 325 milliseconds. The durations of the additional time intervals may be different or the same as the duration of the first time interval. Alternatively, the durations of the first and the second time intervals may be the same.

A delay period 350 may be established between the end of one time interval 330 and the beginning of another time interval 340. The duration of the delay may be in a range of about 0 milliseconds (no delay) to about 40 milliseconds, for example. The cardiac response to the pacing stimulation 310 may be classified based on characteristics of the cardiac signal sensed in the first and/or the additional time intervals 330, 340.

Figure 4:
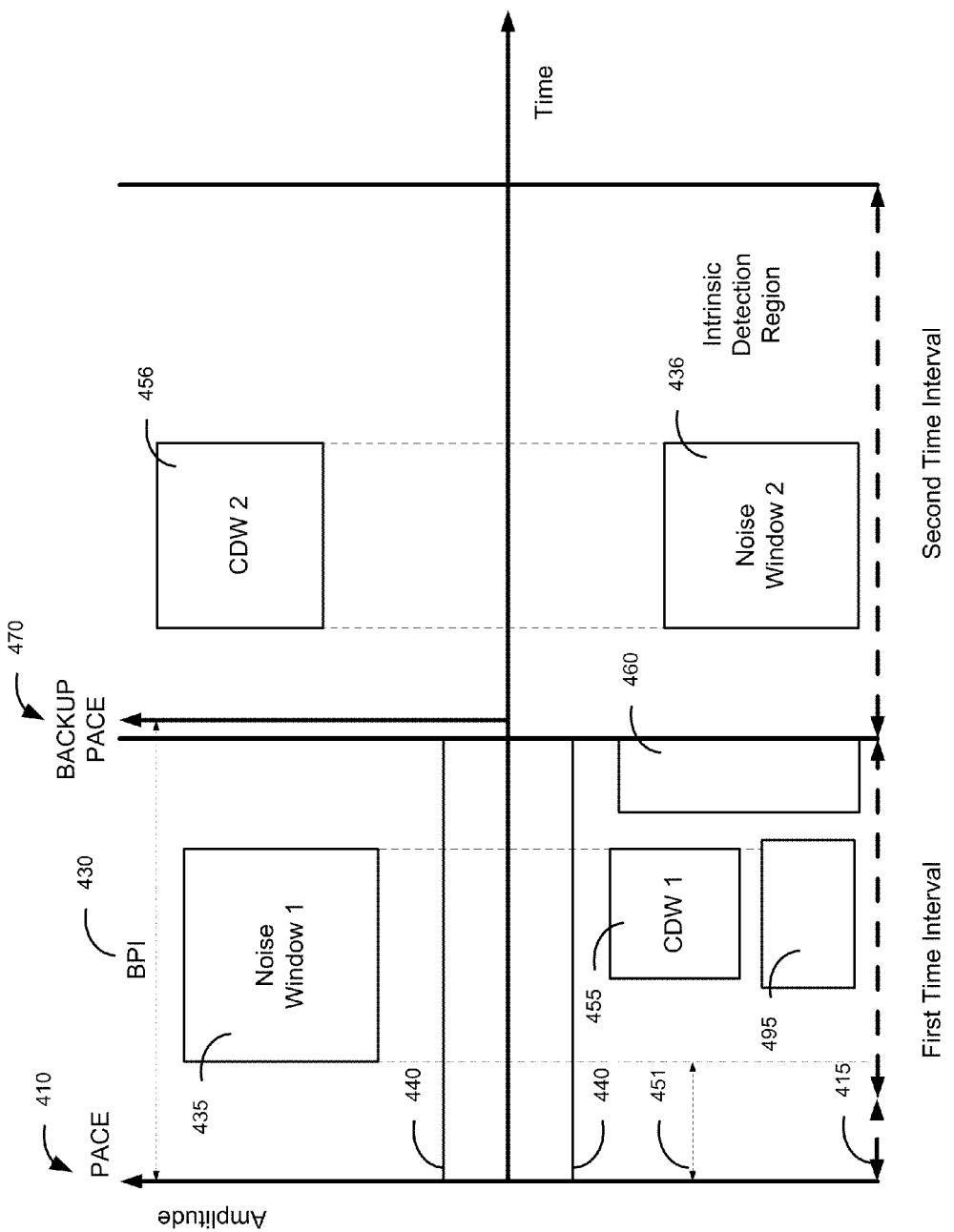
FIG. 4 is a graph including cardiac response detection windows and noise detection windows that may be adapted in accordance with embodiments of the invention.

FIG. 4 illustrates cardiac response classification windows that may be utilized for cardiac devices and methods that discriminate between capture, noncapture, fusion, and noncapture with intrinsic activation, during evoked response detection, and that may be adapted in accordance with embodiments of the invention. Following delivery of a pace 410, the sensing system is blanked, e.g., the sense electrodes are disconnected from sense amplifiers or the sense amplifiers are rendered inoperative, during a blanking period 415. Following the blanking period, the cardiac signal is sensed in one or more time intervals. As illustrated in FIG. 4, sensing may occur in two time intervals 420, 450 following the pacing pulse 410.

In some scenarios, the second 450 and subsequent time intervals (not shown) may be triggered by events occurring in one or more previous intervals. In various implementations, sensing may be performed using the same electrode combination that was used to deliver the pacing stimulation. In other implementations, the pacing stimulation may be delivered using a first electrode configuration and sensing may use a second electrode configuration. Systems and methods for classifying a cardiac response to pacing using multiple time intervals and various sensing and pacing vectors are described in commonly owned U.S. Patent application publications: US 2005/0131476 (Kim et al.), issued as U.S. Pat. No. 7,319,900 (Kim et al.); US 2005/0131477 (Meyer et al.); and US 2005/0131478 (Kim et al.); which are hereby incorporated herein by reference.

During the first time interval 420, the system senses for a cardiac signal magnitude above a threshold level 440. If the cardiac signal does not exceed the threshold 440 during the first time interval 420, then the cardiac response is classified as noncapture and a backup pace 470 may be delivered. The backup pace 470 is typically a high energy pace that is delivered following a backup interval 430. For example, the backup interval 430 may include an interval of about 100 ms timed from the delivery of the primary pace 410.

The system may utilize one or more cardiac response classification windows 455, 456, 460, 495 as illustrated in FIG. 4. An adaptive window method in accordance with embodiments of the invention involves determining if one or more peak values of the cardiac response signal falls, or does not fall, within one or more cardiac response classification windows 455, 456, 460, 495. The cardiac response detection windows 455, 456, 460, and 495 are areas defined in terms of amplitude and time. In other embodiments, different or additional parameters may be used in addition to, or in place of the parameters of amplitude and time.

For this example, the system may classify a cardiac response as capture if a peak value of the cardiac signal is detected in the first capture detection window 455 and a peak value of the cardiac signal is detected in the second capture detection window 456. If a cardiac signal peak is detected in the first non-captured intrinsic detection window 460, or the second non-captured intrinsic detection window 495, the cardiac response may be classified as noncapture with non-captured intrinsic activation. Otherwise, the beat is classified as a fusion/pseudofusion beat, or further discriminated. Depending on the cardiac response's classification, one or more windows associated with the classification may be adapted.

Devices and methods in accordance with embodiments of the present invention may involve the use of one or more noise detection windows 435, 436 for further discrimination of cardiac waveforms. If signal peaks fall within the cardiac response classification windows 455, 456, 460, 495 then the system may check for peaks opposite in polarity and comparable in magnitude to the cardiac response signal peaks. FIG. 4 illustrates detection windows 435, 436 in the first and the second time intervals 420, 450. The detection windows 435, 436 may be any shape or size, and the shape and size may also be adaptable in accordance with the present invention. For example, the detection windows 435, 436 may be the same size and/or shape as a corresponding capture detection window 455, 456 in a particular time interval 420, 450, or may be a different size and/or shape. Formation of detection windows, aspects of which may be utilized in the approaches of the present invention are described in commonly owned U.S. Pat. No. 7,499,751 (Meyer et al.) which is incorporated herein by reference, and U.S. Pat. No. 7,477,932 (Lee et al.), which is incorporated herein by reference.

Figure 5:
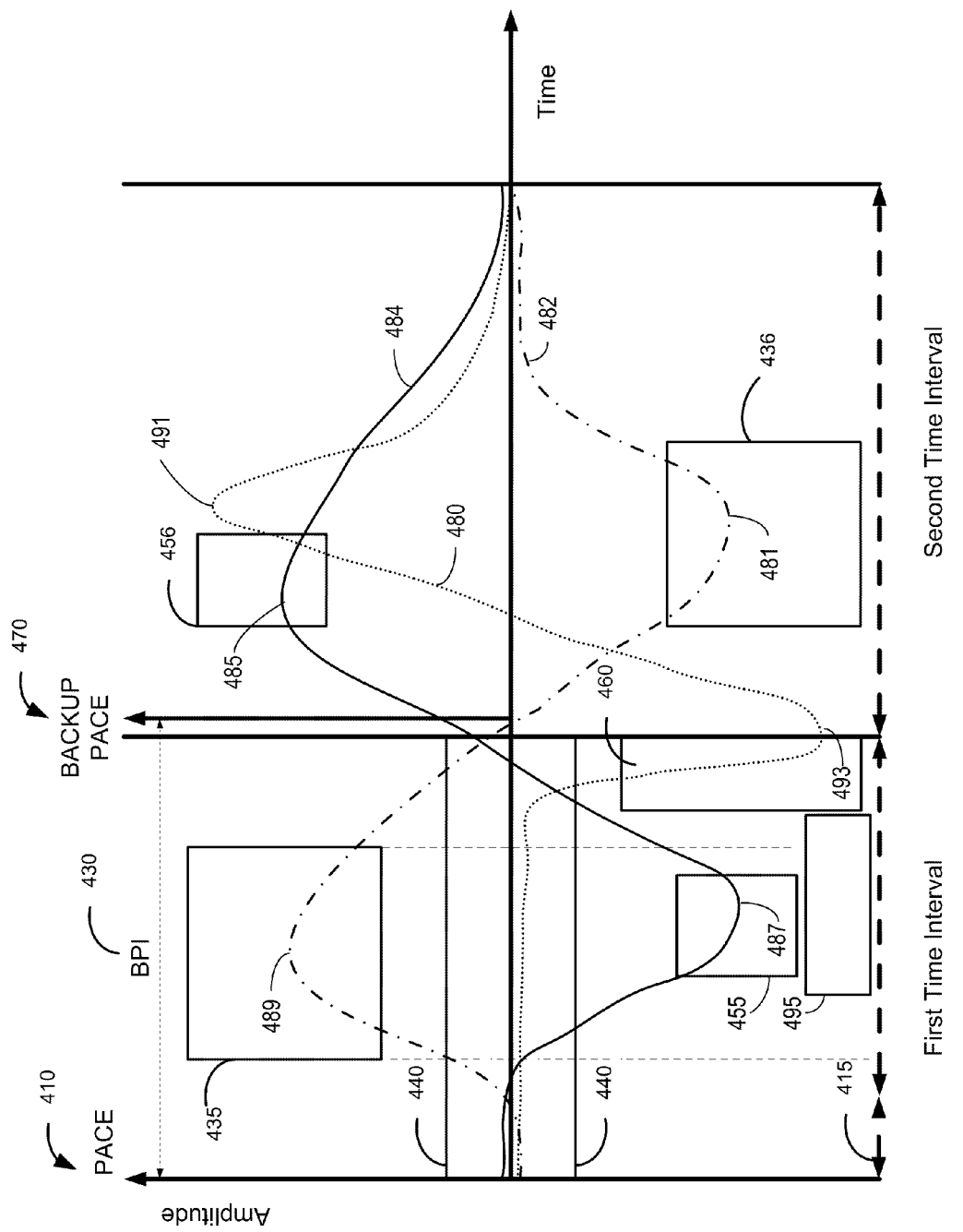
FIG. 5 illustrates cardiac response waveform portions superimposed over the graph in FIG. 4 in accordance with embodiments of the invention.

FIG. 5 illustrates three representative cardiac response waveform portions superimposed over the graph illustrated in FIG. 4. A non-captured intrinsic beat 480, a PVC beat 482, and a captured beat 484 are drawn, illustrating waveform parameters useful for adapting windows for cardiac waveform discrimination during cardiac response detection in accordance with the present invention. The waveform parameters of the PVC beat 482 illustrated in the graph of FIG. 5 include, but are not limited to, a negative peak amplitude 481 within the noise window 436 during the second time interval 450, and a positive peak 489 within the noise window 435 during the first time interval 420. The waveform parameters of the non-captured intrinsic beat 480 illustrated in the graph of FIG. 5 include, but are not limited to, a positive peak amplitude 491 within the second time interval 450 and a negative peak amplitude 493 within the response classification window 460. The waveform parameters of the captured beat 484 illustrated in the graph of FIG. 5 include, but are not limited to, a negative peak amplitude 487 within the response classification window 455 during the first time interval 420, and a positive peak 485 within the response classification window 456 during the second time interval 450.

As evident in FIG. 5, the non-captured intrinsic beat 480 and the captured beat 484 have morphologies similar enough that they may be confused if discrimination of non-captured intrinsic beats during evoked response detection and classification is not performed. Providing adaptive windowing in accordance with the present invention improves the discrimination capabilities of cardiac devices by allowing closer spacing of windows and smaller window sizes, and reduces or eliminates the inclusion of undesired response signals during capture threshold testing, capture verification, template initialization and/or updating, and/or for other purposes when cardiac response signal features vary over time.

The embodiments of the present system illustrated herein are generally described as being implemented in a patient implantable medical device (PIMD) such as a pacemaker/defibrillator (PD) that may operate in numerous pacing modes known in the art. Various types of single and multiple chamber implantable cardiac pacemaker/defibrillators are known in the art and may be used in connection with cardiac devices and methods that provide adaptive windowing during evoked response detection and classification in accordance with the present invention. The methods of the present invention may also be implemented in a variety of implantable or patient-external cardiac rhythm management devices, including single and multi chamber pacemakers, defibrillators, cardioverters, bi-ventricular pacemakers, cardiac resynchronizers, and cardiac monitoring systems, for example.

Although the present system is described in conjunction with an implantable cardiac pacemaker/defibrillator having a microprocessor-based architecture, it will be understood that the implantable pacemaker/defibrillator (or other device) may be implemented in any logic-based integrated circuit architecture, if desired.

Figure 6:
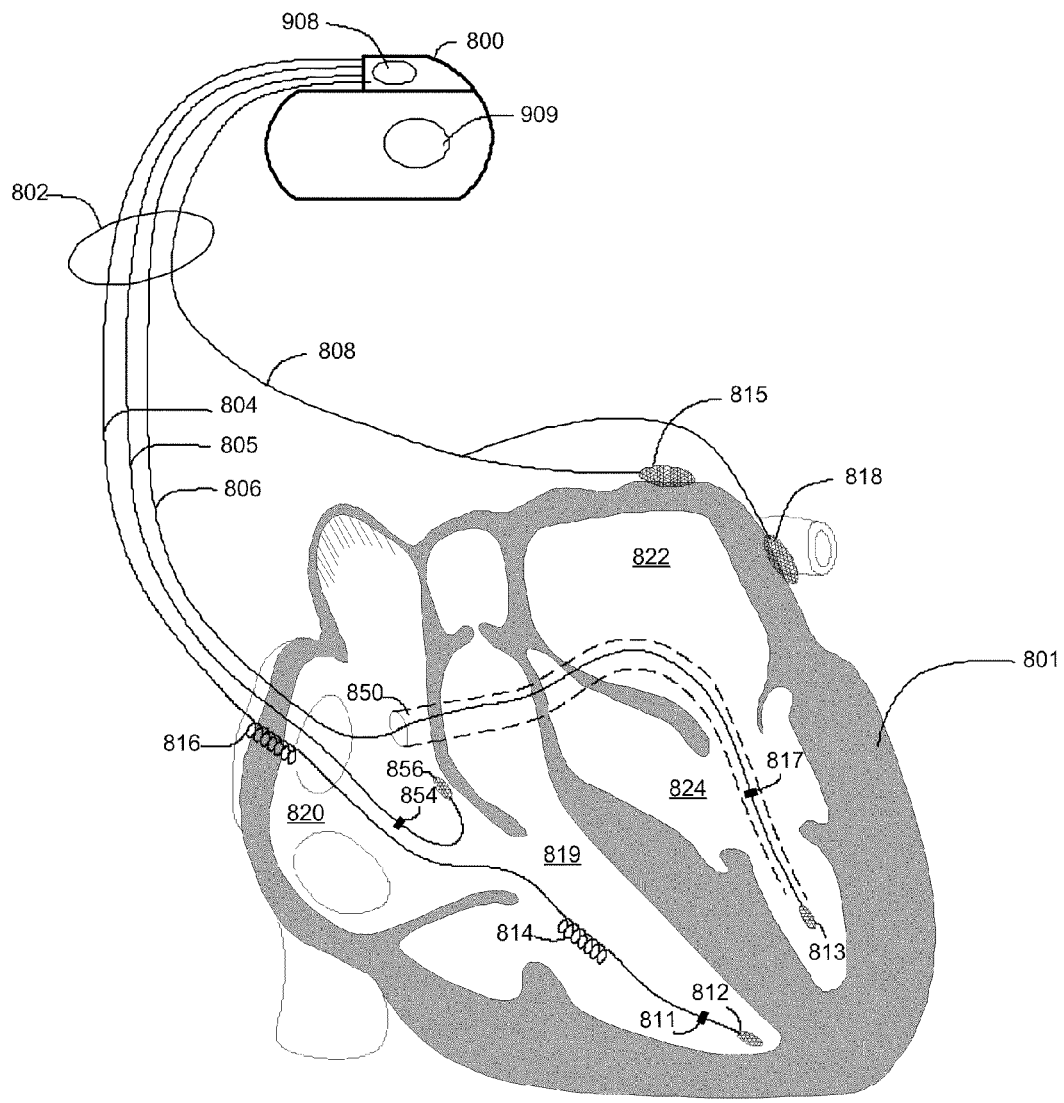
FIG. 6 is a partial view of one embodiment of an implantable medical device that may use adaptive windows for cardiac waveform discrimination in accordance with embodiments of the invention.

Referring now to FIG. 6 of the drawings, there is shown a cardiac rhythm management system that may be used to implement detection window adaptation in accordance with the present invention. The cardiac rhythm management system in FIG. 6 includes a pacemaker/defibrillator 800 electrically and physically coupled to a lead system 802. The housing and/or header of the pacemaker/defibrillator 800 may incorporate one or more electrodes 908, 909 used to provide electrical stimulation energy to the heart and to sense cardiac electrical activity. The pacemaker/defibrillator 800 may utilize all or a portion of the pacemaker/defibrillator housing as a can electrode 909. The pacemaker/defibrillator 800 may include an indifferent electrode 908 positioned, for example, on the header or the housing of the pacemaker/defibrillator 800. If the pacemaker/defibrillator 800 includes both a can electrode 909 and an indifferent electrode 908, the electrodes 908, 909 typically are electrically isolated from each other.

The lead system 802 is used to detect electric cardiac signals produced by the heart 801 and to provide electrical energy to the heart 801 under certain predetermined conditions to treat cardiac arrhythmias. The lead system 802 may include one or more electrodes used for pacing, sensing, and/or defibrillation. In the embodiment shown in FIG. 6, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 6 illustrates one embodiment that may be used in connection with the adaptive detection windowing methodologies described herein. Other leads and/or electrodes may additionally or alternatively be used.

The lead system 802 may include intracardiac leads 804, 805, 806 implanted in a human body with portions of the intracardiac leads 804, 805, 806 inserted into a heart 801. The intracardiac leads 804, 805, 806 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 6, the lead system 802 may include one or more extracardiac leads 808 having electrodes, e.g., epicardial electrodes, positioned at locations outside the heart for sensing and pacing one or more heart chambers.

The right ventricular lead system 804 illustrated in FIG. 6 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart 801. The SVC-coil 816 is positioned at an appropriate location within the right atrium chamber 820 of the heart 801 or a major vein leading to the right atrial chamber 820 of the heart 801.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824, which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the pacemaker/defibrillator 800, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 805 includes an RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

FIG. 6 illustrates one embodiment of a left atrial lead system 808. In this example, the left atrial lead 808 is implemented as an extracardiac lead with LA distal 818 and LA proximal 815 electrodes positioned at appropriate locations outside the heart 801 for sensing and pacing the left atrium 822. Unipolar pacing and/or sensing of the left atrium may be accomplished, for example, using the LA distal electrode 818 to the can 909 pacing vector. The LA proximal 815 and LA distal 818 electrodes may be used together to implement bipolar pacing and/or sensing of the left atrium 822.

Figure 7:
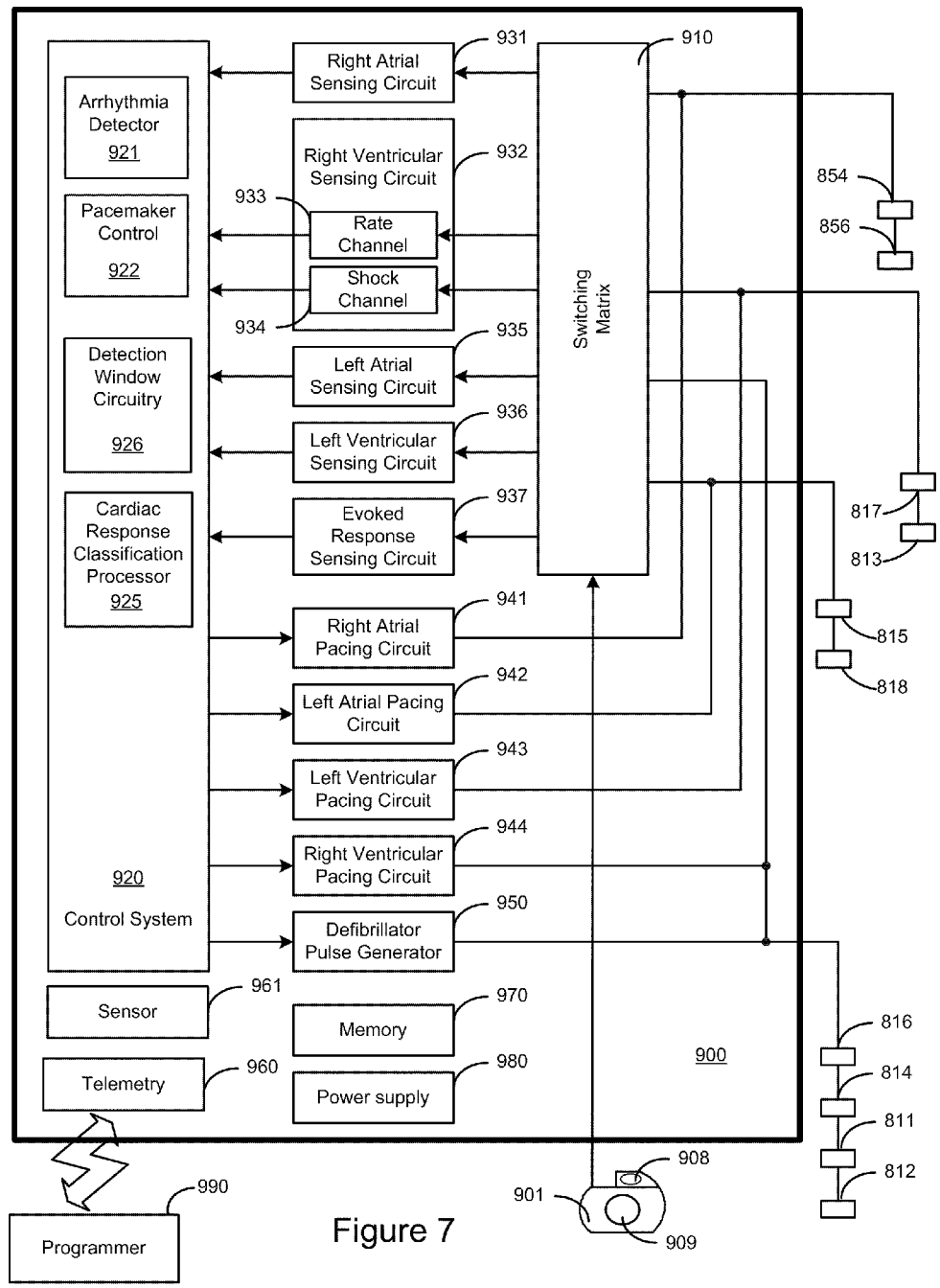
FIG. 7 is a block diagram of an implantable medical device that may use adaptive windows for cardiac waveform discrimination in accordance with embodiments of the invention.

Referring now to FIG. 7, there is shown an embodiment of a cardiac pacemaker/defibrillator 900 suitable for implementing detection window adaptation methods of the present invention. FIG. 7 shows a cardiac pacemaker/defibrillator 900 divided into functional blocks. It is understood by those skilled in the art that there exist many possible configurations in which these functional blocks can be arranged. The example depicted in FIG. 7 is one possible functional arrangement. Other arrangements are also possible. For example, more, fewer, or different functional blocks may be used to describe a cardiac pacemaker/defibrillator suitable for implementing the methodologies for detection window adaptation and cardiac response classification in accordance with the present invention. In addition, although the cardiac pacemaker/defibrillator 900 depicted in FIG. 7 contemplates the use of a programmable microprocessor-based logic circuit, other circuit implementations may be utilized.

The cardiac pacemaker/defibrillator 900 depicted in FIG. 7 includes circuitry for receiving cardiac signals from a heart and delivering electrical stimulation energy to the heart in the form of pacing pulses or defibrillation shocks. In one embodiment, the circuitry of the cardiac pacemaker/defibrillator 900 is encased and hermetically sealed in a housing 901 suitable for implanting in a human body. Power to the cardiac pacemaker/defibrillator 900 is supplied by an electrochemical battery 980. A connector block (not shown) is attached to the housing 901 of the cardiac pacemaker/defibrillator 900 to allow for the physical and electrical attachment of the lead system conductors to the circuitry of the cardiac pacemaker/defibrillator 900.

The cardiac pacemaker/defibrillator 900 may be a programmable microprocessor-based system, including a control system 920 and a memory 970. The memory 970 may store parameters for various pacing, defibrillation, and sensing modes, along with other parameters. Further, the memory 970 may store data indicative of cardiac signals received by other components of the cardiac pacemaker/defibrillator 900. The memory 970 may be used, for example, for storing historical EGM and therapy data. The historical data storage may include, for example, data obtained from long-term patient monitoring used for trending and/or other diagnostic purposes. Historical data, as well as other information, may be transmitted to an external programmer unit 990 as needed or desired.

The control system 920 and memory 970 may cooperate with other components of the cardiac pacemaker/defibrillator 900 to control the operations of the cardiac pacemaker/defibrillator 900. The control system 920 depicted in FIG. 7 incorporates detection window circuitry 926 configured to provide and adapt detection windows as previously described in accordance with embodiments of the invention.

The control system 920 further includes a cardiac response classification processor 925 for classifying cardiac responses to pacing stimulation. The cardiac response classification processor performs the function of analyzing the location of cardiac signal features with respect to one or more detection window boundaries to determine the cardiac response to pacing.

The control system 920 may include additional functional components including a pacemaker control circuit 922, an arrhythmia detector 921, along with other components for controlling the operations of the cardiac pacemaker/defibrillator 900.

Telemetry circuitry 960 may be implemented to provide communications between the cardiac pacemaker/defibrillator 900 and an external programmer unit 990. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the cardiac pacemaker/defibrillator 900 from the programmer unit 990 during and after implant. In addition, stored cardiac data pertaining to capture threshold, capture detection, and/or cardiac response classification, for example, along with other data, may be transferred to the programmer unit 990 from the cardiac pacemaker/defibrillator 900.

The telemetry circuitry 960 may provide for communication between the cardiac pacemaker/defibrillator 900 and an advanced patient management (APM) system. The advanced patient management system allows physicians or other personnel to remotely and automatically monitor cardiac and/or other patient conditions. In one example, a cardiac pacemaker/defibrillator, or other device, may be equipped with various telecommunications and information technologies that enable real-time data collection, diagnosis, and treatment of the patient. Various embodiments described herein may be used in connection with advanced patient management.

Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

In the embodiment of the cardiac pacemaker/defibrillator 900 illustrated in FIG. 7, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the defibrillation electrodes are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration, the can electrode 909 and the SVC-coil electrode 816 may be electrically shorted and an RV shock channel signal may be detected as the voltage developed between the RV-coil 814 and the can electrode 909/SVC-coil 816 combination.

Outputs from the right ventricular sensing circuit 932 are coupled to the control system 920. In one embodiment of the invention, rate channel signals and shock channel signals may be used to develop morphology templates for analyzing cardiac signals. In this embodiment, rate channel signals and shock channel signals may be transferred from the right ventricular sensing circuit 932 to the control system 920 and analyzed for arrhythmia detection.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to the can 909 vector or the LA proximal electrode 815 to the can 909 vector.

A left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent to the left heart. Signals detected using combinations of the LV electrodes 813, 817, LV coil electrode (not shown), and/or the can electrode 909 may be sensed and amplified by the left ventricular sensing circuitry 936. The output of the left ventricular sensing circuit 936 is coupled to the control system 920.

The outputs of the switching matrix 910 may be operated to couple selected combinations of electrodes 811, 812, 813, 814, 815, 816, 817, 818, 856, 854 to an evoked response sensing circuit 937. The evoked response sensing circuit 937 serves to sense and amplify voltages developed using various combinations of electrodes for discrimination of various cardiac responses to pacing in accordance with embodiments of the invention. The cardiac response classification processor 925 may cooperate with detection window circuitry 926 to analyze the output of the evoked response sensing circuit 937 for implementation of cardiac pacing response classification.

Various combinations of pacing and sensing electrodes may be utilized in connection with pacing and sensing the cardiac signal following the pace pulse to classify the cardiac response to the pacing pulse. For example, in some embodiments, a first electrode combination is used for pacing a heart chamber and a second electrode combination is used to sense the cardiac signal following pacing. In other embodiments, the same electrode combination is used for pacing and sensing. Use of different electrodes for pacing and sensing in connection with capture verification is described in commonly owned U.S. Pat. No. 6,128,535, which is incorporated herein by reference.

The pacemaker control circuit 922, in combination with pacing circuitry for the left atrium, right atrium, left ventricle, and right ventricle 941, 942, 943, 944, may be implemented to selectively generate and deliver pacing pulses to the heart using various electrode combinations. The pacing electrode combinations may be used to effect bipolar or unipolar pacing pulses to a heart chamber using one of the pacing vectors as described above. In some implementations, the cardiac pacemaker/defibrillator 900 may include a sensor 961 that is used to sense the patient's hemodynamic need. In one implementation, the sensor may comprise, for example, an accelerometer configured to sense patient activity. In another implementation, the sensor may comprise an impedance sensor configured to sense patient respiration. The pacing output of the cardiac pacemaker/defibrillator may be adjusted based on the sensor 961 output.

The electrical signal following the delivery of the pacing pulses may be sensed through various sensing vectors coupled through the switch matrix 910 to the evoked response sensing circuit 937 and/or other sensing circuits and used to classify the cardiac response to pacing. The cardiac response may be classified as one of a captured response, a non-captured response, a non-captured response with intrinsic activation, and a fusion/pseudofusion beat, for example.

Subcutaneous electrodes may provide additional sensing vectors useable for cardiac response classification. In one implementation, a cardiac rhythm management system may involve a hybrid system including an intracardiac device configured to pace the heart and an extracardiac device, e.g., a subcutaneous defibrillator, configured to perform functions other than pacing. The extracardiac device may be employed to detect and classify the cardiac response to pacing based on signals sensed using subcutaneous electrode arrays. The extracardiac and intracardiac devices may operate cooperatively with communication between the devices occurring over a wireless link, for example. Examples of subcutaneous electrode systems and devices are described in commonly owned U.S. Patent Application Publications US 2004/0230229 (Lovett et al.) and US 2004/0230230 (Lindstrom et al.), which are hereby incorporated herein by reference in their respective entireties.

The components, functionality, and structural configurations depicted herein are intended to provide an understanding of various features and combination of features that may be incorporated in an implantable pacemaker/defibrillator. It is understood that a wide variety of cardiac monitoring and/or stimulation device configurations are contemplated, ranging from relatively sophisticated to relatively simple designs. As such, particular cardiac device configurations may include particular features as described herein, while other such device configurations may exclude particular features described herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac device, comprising:
   sensing a cardiac signal that follows a pacing pulse;
   detecting at least one feature of the cardiac signal;
   comparing the cardiac signal feature to a detection window;
   determining a cardiac response to the pacing pulse based on comparison of the cardiac signal feature to the detection window;
   prior to the comparison of the cardiac signal feature to the detection window, defining a preferred direction for modifying the detection window;
   modifying the detection window more aggressively toward the cardiac signal feature if the preferred direction is toward the cardiac signal feature and modifying the detection window less aggressively toward the cardiac signal feature if the preferred direction is not toward the cardiac signal feature;
   using the modified detection window to determine a subsequent cardiac pacing response to a subsequent pacing pulse; and
   delivering pacing therapy based on the cardiac pacing response.

2. The method of claim 1, wherein a first reference value is associated with the detection window, wherein the cardiac signal feature has a first coordinate, and wherein the comparing comprises comparing the first coordinate to the first reference value.

3. The method of claim 2, wherein the first reference value is a temporal reference value, and wherein the first coordinate is a temporal coordinate.

4. The method of claim 2, wherein the first reference value is an amplitude reference value, and wherein the first coordinate is an amplitude coordinate.

5. The method of claim 1, wherein the modifying is carried out in response to the comparing.

6. The method of claim 5, wherein the detection window has boundaries associated therewith, and wherein the modifying is carried out provided that the cardiac signal feature falls within the boundaries.

7. The method of claim 6, wherein the modifying is carried out provided further that the cardiac signal feature is greater than a predetermined distance from one or more of the boundaries.

8. The method of claim 1, wherein the detection window has a lower bound and an upper bound, and wherein modifying the detection window comprises modifying at least one of the lower and upper bounds.

9. The method of claim 8, wherein modifying the detection window comprises modifying only one of the lower and upper bounds.

10. A system, comprising:
a pulse generator configured to generate pacing pulses for delivery to a heart;
a sensing system configured to sense a cardiac signal following a pacing pulse delivered to the heart, the cardiac signal associated with a type of cardiac response to the pacing pulse; and
a processor coupled to the sensing system, the processor configured to:
detect at least one feature of the cardiac signal;
to preferentially adjust the detection window based on a location of the cardiac signal feature;
define a preferred direction for modifying the detection window, and thereafter compare the cardiac signal feature to the detection window;
determine a cardiac response to the pacing pulse based on the comparison of the cardiac signal feature to the detection window;
modify the detection window more aggressively toward the cardiac signal feature if the preferred direction is toward the cardiac signal feature and modify the detection window less aggressively toward the cardiac signal feature if the preferred direction is not toward the cardiac signal feature; and
use the modified detection window to determine a subsequent cardiac pacing response to a subsequent pacing pulse; and
a therapy delivery unit configured to deliver pacing therapy to the heart based on the cardiac pacing response.

11. The system of claim 10, wherein a first reference value is associated with the detection window, wherein the cardiac signal feature has a first coordinate, and wherein the processor is configured to compare the first coordinate to the first reference value.

12. The system of claim 11, wherein the first reference value is a temporal reference value, and wherein the first coordinate is a temporal coordinate.

13. The system of claim 11, wherein the first reference value is an amplitude reference value, and wherein the first coordinate is an amplitude coordinate.

14. The system of claim 10, wherein the processor is configured to modify the detection window in response to the comparison of the cardiac signal feature to the detection window.

15. The system of claim 14, wherein the detection window has boundaries associated therewith, and wherein the processor is configured to modify the detection window provided that the cardiac signal feature falls within the boundaries.

16. The system of claim 15, wherein the processor is configured to modify the detection window provided further that the cardiac signal feature is greater than a predetermined distance from one or more of the boundaries.

17. The system of claim 10, wherein the detection window has a lower bound and an upper bound, and wherein the processor is configured to modify the detection window by modifying at least one of the lower and upper bounds.

18. The system of claim 17, wherein the processor is configured to modify the detection window by modifying only one of the lower and upper bounds.

19. The system of claim 10, wherein the detection window comprises a capture detection window used to determine whether the cardiac response to the pacing pulse comprises a captured beat.

20. The system of claim 10, wherein the processor is configured to modify the detection window provided that modification of the detection window does not exceed a predetermined range.

21. A system, comprising:
means for delivering pacing pulses to a heart;
means for sensing a cardiac signal that follows a pacing pulse delivered to the heart;
means for detecting at least one feature of the cardiac signal;
means for comparing the cardiac signal feature to a detection window;
means for determining a cardiac response to the pacing pulse based on comparison of the cardiac signal feature to the detection window;
means for defining, prior to the comparison of the cardiac signal feature to the detection window, a preferred direction for modifying the detection window;
means for modifying the detection window more aggressively toward the cardiac signal feature if the preferred direction is toward the cardiac signal feature and for modifying the detection window less aggressively toward the cardiac signal feature if the preferred direction is not toward the cardiac signal feature;
means for using the modified detection window to determine a subsequent cardiac pacing response to a subsequent pacing pulse; and
means for delivering pacing therapy to the heart based on the cardiac pacing response.

* * * * *